United States Patent
Roeder

(10) Patent No.: US 9,375,307 B2
(45) Date of Patent: Jun. 28, 2016

(54) GRAFT FABRIC CRIMPING PATTERN

(75) Inventor: Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 135 days.

(21) Appl. No.: 12/556,943

(22) Filed: Sep. 10, 2009

(65) Prior Publication Data
US 2010/0106239 A1    Apr. 29, 2010

Related U.S. Application Data

(60) Provisional application No. 61/097,637, filed on Sep. 17, 2008.

(51) Int. Cl.
*A61F 2/07* (2013.01)
*A61F 2/844* (2013.01)
*A61F 2/89* (2013.01)

(52) U.S. Cl.
CPC . *A61F 2/07* (2013.01); *A61F 2/844* (2013.01); *A61F 2/89* (2013.01); *A61F 2002/075* (2013.01); *A61F 2230/005* (2013.01)

(58) Field of Classification Search
CPC ...... A61F 2/07; A61F 2002/075; A61F 2/844
USPC ................. 623/1.13, 1.28, 1.32, 1.33, 1.44, 623/1.49–1.54; 606/151, 200
See application file for complete search history.

(56) References Cited

U.S. PATENT DOCUMENTS

| | | | | |
|---|---|---|---|---|
| 5,782,904 | A * | 7/1998 | White et al. | 623/1.13 |
| 5,814,063 | A * | 9/1998 | Freitag | 623/1.13 |
| 6,565,596 | B1 * | 5/2003 | White et al. | 623/1.13 |
| 6,626,938 | B1 * | 9/2003 | Butaric et al. | 623/1.28 |
| 6,911,040 | B2 * | 6/2005 | Johnson et al. | 623/1.13 |
| 7,060,092 | B2 * | 6/2006 | Kuribayashi et al. | 623/1.29 |
| 2006/0265052 | A1 * | 11/2006 | You | 623/1.22 |
| 2008/0262594 | A1 * | 10/2008 | Morris | 623/1.13 |
| 2009/0125095 | A1 * | 5/2009 | Bui et al. | 623/1.13 |

* cited by examiner

*Primary Examiner* — Sarah W Aleman
(74) *Attorney, Agent, or Firm* — Brinks Gilson & Lione

(57) ABSTRACT

A pattern of graft material that allows for radial expansion and contraction that comprises a plurality of rows of folds with an undulating configuration with at least one apex and at least one trough and the rows of folds each have a ridge and a valley therein. At least one stent with an undulating configuration can be attached to the at least one row of folds.

15 Claims, 4 Drawing Sheets

GRAFT FABRIC CRIMPING PATTERN

CROSS-REFERENCE TO RELATED APPLICATIONS

This application claims the benefit of U.S. Provisional Application No. 61/097,637, filed Sep. 17, 2008, which is incorporated by reference in its entirety.

TECHNICAL FIELD

The present invention relates to flexible stent graft fabric patterns and their use on an endoluminal prosthesis.

BACKGROUND

Origami is the ancient Japanese art of paper folding. Using a sheet of paper, geometric and intricate folds are made to represent objects usually found in nature, such as a crane or flower. Although paper was exclusively used in this art in the past, modern technology has made available other materials such as aluminum foil and materials made of natural and synthetic fibers. Origami art has usually served a purely aesthetic purpose and industrial uses are not that well known.

Over the past 10 years, endovascular aneurysm repair has become the treatment of choice for abdominal aortic aneurysms (AAA) with favorable post-op results compared to open repair. The move from open to endovascular treatments of AAA has involved a significant learning curve that has exposed specific problems and complications. Iliac artery elongation, tortuosity, and dilation are common in patients with aortic aneurysms. The loss of elastin may reduce support within the artery, thus leading to elongation and tortuosity, even in non-aneurysmal parts of the artery. Stent grafts and other endoluminal prosthetics have difficulty providing stability and form when implanted in such tortuous settings.

BRIEF SUMMARY

Herein provided is an endoluminal prosthesis of tubular graft material having a proximal end and a distal end, the graft material comprising a plurality of rows of folds that extend transversely around the prosthesis in a undulating pattern. At least one stent is attached to at least one row of folds and the rows of folds allow for radial expansion and contraction of the prosthesis.

Another aspect of the prosthesis described herein is a pattern of folds in a graft material that allow for radial expansion and contraction comprising a plurality of rows of folds having a undulating configuration with at least one apex and at least one trough. The rows of folds each comprise a ridge and a valley therein. The ridge and the valley have a distance separating them that can vary. At least one stent having a undulating configuration with at least one apex and at least one trough can be attached to at least one rows of folds.

BRIEF DESCRIPTION OF THE DRAWINGS

FIG. 1b shows a cross sectional view of the pattern having rows of folds with ridges and valleys.

DETAILED DESCRIPTION OF THE DRAWINGS AND THE PRESENTLY PREFERRED EMBODIMENTS

Figure 1A:
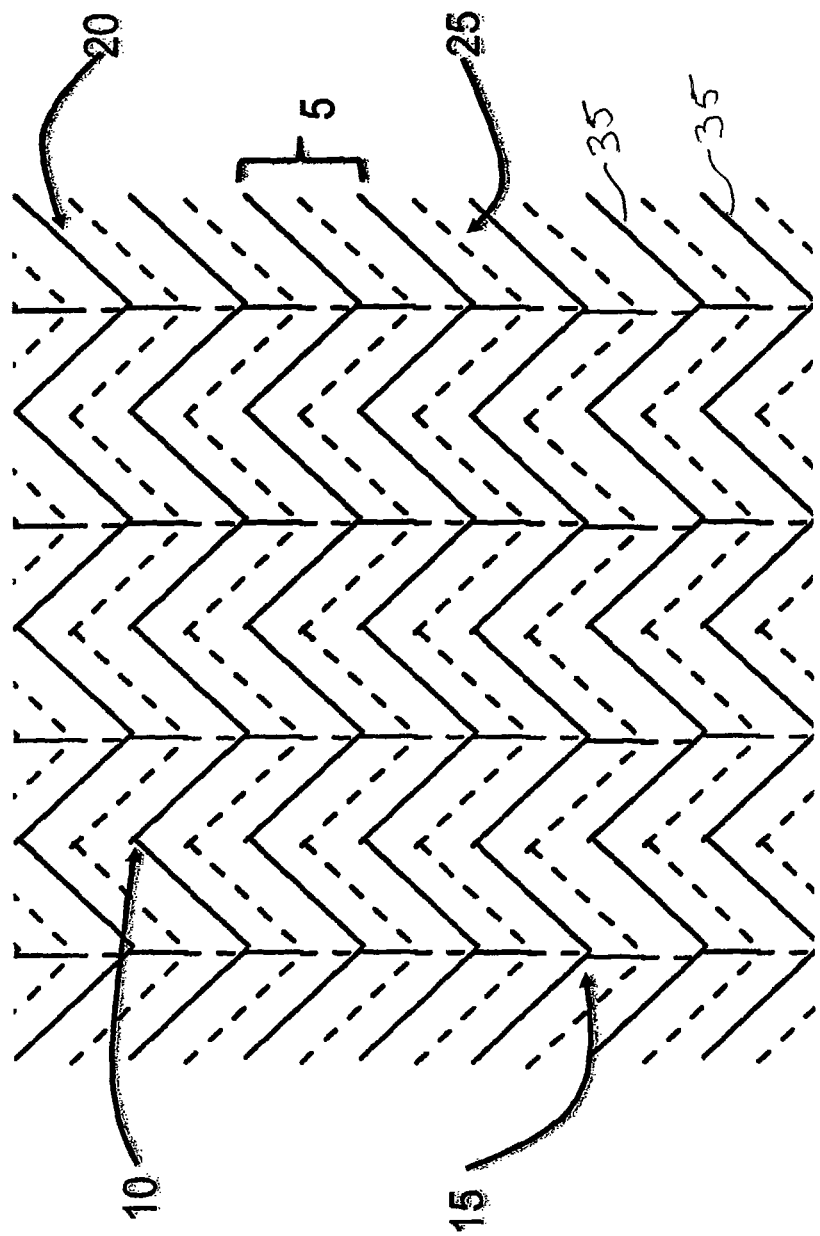
FIG. 1a shows a section of the pattern of graft material having folds as described herein.
Figure 16:
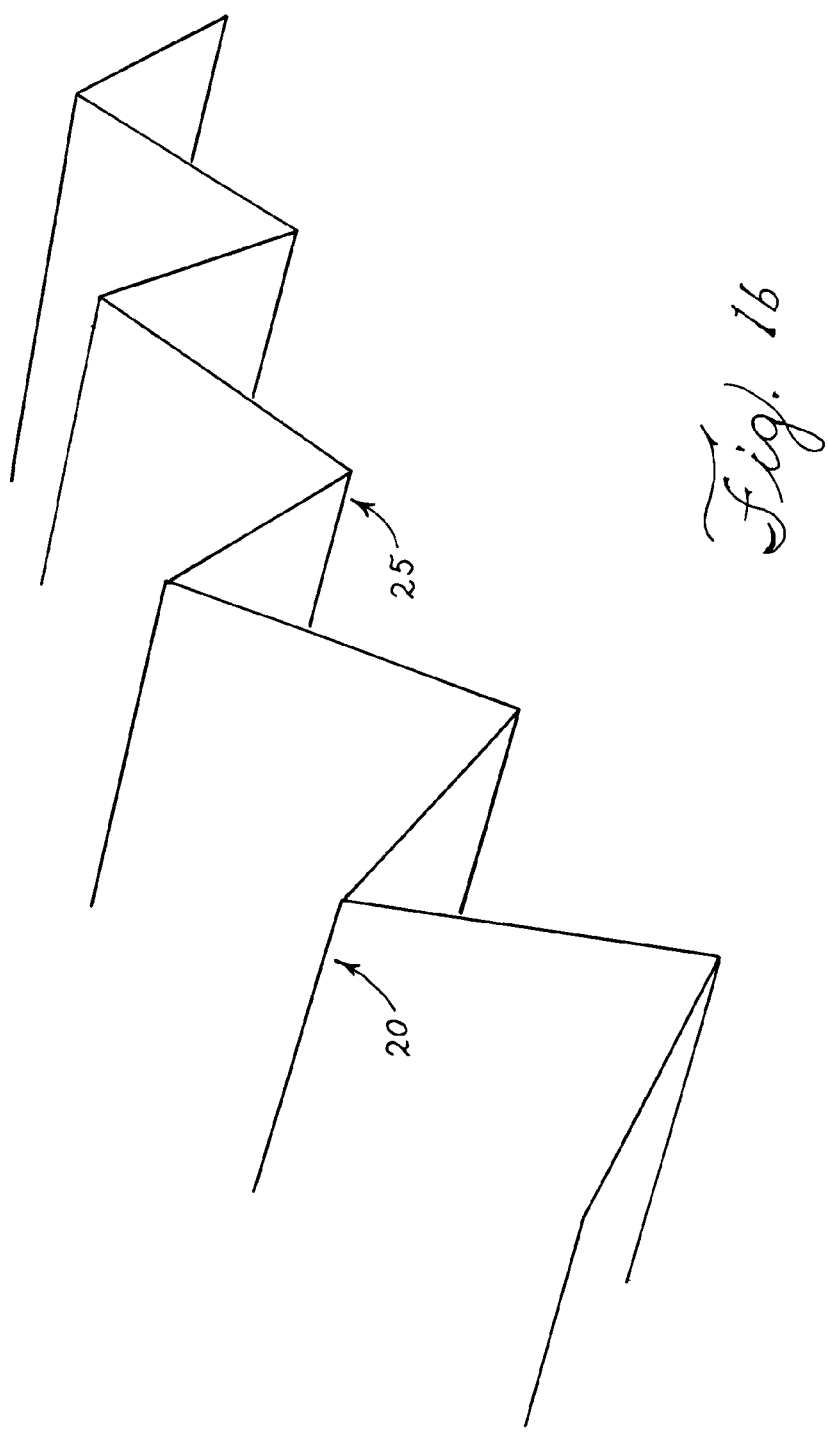

The term "prosthesis" means any replacement for a body part or for a function of that body part or any device that enhances or adds functionality to a physiological system.

The term "stent" means any device that provides rigidity, expansion force, or support to a prosthesis, such as a stent graft. In one configuration, the stent may represent a plurality of discontinuous devices. In another configuration, the stent may represent one device. Stents may have a wide variety of configurations and may be balloon-expandable or self-expanding. Typically, stents have a circular cross-section when fully expanded, so as to conform to the generally circular cross-section of a body lumen. In one example, a stent may comprise struts (elongate portions) and acute bends (curvilinear portions) that are arranged in a zigzag configuration in which the struts are set at angles to each other and are connected by the acute bends. Although an undulating configuration is used throughout this application, it is understood that the stent may have a sinusoidal or a zigzag configuration as well. One example of a stent configuration is a Z-stent. The stents as described in this disclosure may be attached to the exterior of the graft, the interior of the graft, and/or may be sandwiched between two or more layers of graft material.

A variety of biocompatible materials may be employed to construct the stent, or portions of the stent, including metals and/or alloys, medically-acceptable polymers, and/or bioabsorbable polymers or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In a preferred configuration, the stent is constructed from nitinol, stainless steel, and/or cobalt-chromium alloys.

The term "graft or graft material" means a generally cannular or tubular member which acts as an artificial vessel or prosthesis. A graft by itself or with the addition of other elements, such as structural components, can be an endoluminal prosthesis. The graft comprises a single material, a blend of materials, a weave, a laminate, or a composite of two or more materials.

The graft material is a biocompatible material that is both flexible and abrasion resistant. The material can comprise woven, non-woven, braided, or knitted material. Furthermore, the graft material should be selected from those materials that are particularly well suited for thermoplastic deformation, such that the material can be thermoplastically fused to a stent. Preferably, the woven graft material is a woven polyester. More preferably, the woven graft material is a polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

Other suitable materials comprise biocompatible polyurethane, silicone infused polyurethane, such as Thoralon®

(Thoratec, Pleasanton, Calif.), or Biospan®, Bionate®, Elasthane®, Pursil® and Carbosil® (Polymer Technology Group, Berkeley, Calif.). In some embodiments, the graft also can comprise SIS. The graft material can comprise a single biologically active material or a blend of materials that are thromboresistant with or without the addition of foams, adhesives, or polymers.

Thoralon® has been used in certain vascular applications and is characterized by thromboresistance, high tensile strength, low water absorption, low critical surface tension, and good flex life. Thoralon® is believed to be biostable and to be useful in vivo in long-term blood contacting applications requiring biostability and leak resistance. Because of its flexibility, Thoralon® is useful in larger vessels, such as the abdominal aorta, where elasticity and compliance is beneficial.

As represented in FIG. 1a, herein disclosed is a pattern of rows 5 of folds in a graft material that allow for radial expansion and contraction. The pattern comprises a plurality of rows 5 of folds having an undulating configuration with at least one apex 10 and at least one trough 15. The rows 5 of folds each comprise a ridge 20 and a valley 25 therein. As illustrated in FIG. 1a, the ridge 20 of the row 5 of folds is represented as a solid line and the valley 25 is represented as a dashed line. FIG. 1b is an illustration of a cross section of a sheet of graft material having the pattern. The ridges 20 are upwardly pointing folds and the valleys 25 point downward as seen in FIG. 1b. The ridges 20 are outwardly pointing folds when viewing the pattern on a tubular prosthesis while the valleys 25 point inward. The ridges 20 and valleys 25 can be preferably parallel to one another and alternate along the pattern.

The graft material can be crimped or folded in such a way that stents can be attached or integrated into the formed pattern. The flexibility of the resulting prosthesis is enhanced also by the methods of folding. A prosthesis having graft material folded as described herein is collapsible. The collapsibility is maintained even when a stent is combined with it. As such, the pattern of the present invention further comprises at least one stent 35 that has an undulating configuration similar to the configuration of the rows 5 of folds. It may be preferred that a Z-stent is used whose curvature mirrors the undulating configuration of the rows 5 of folds. The stent 35 can further have at least one apex and at least one trough. The stent 35, or multiple stents, can be attached to one row 5 of folds along the ridge 20 of the row of folds or, if multiple stents are used, along the ridges of a number of rows 5 of folds. At least two stents can be attached to at least two rows. The stents can be attached to nonconsecutive rows as well. Attaching the stents to every second or third row can increase the compressibility of graft material.

Figure 2:
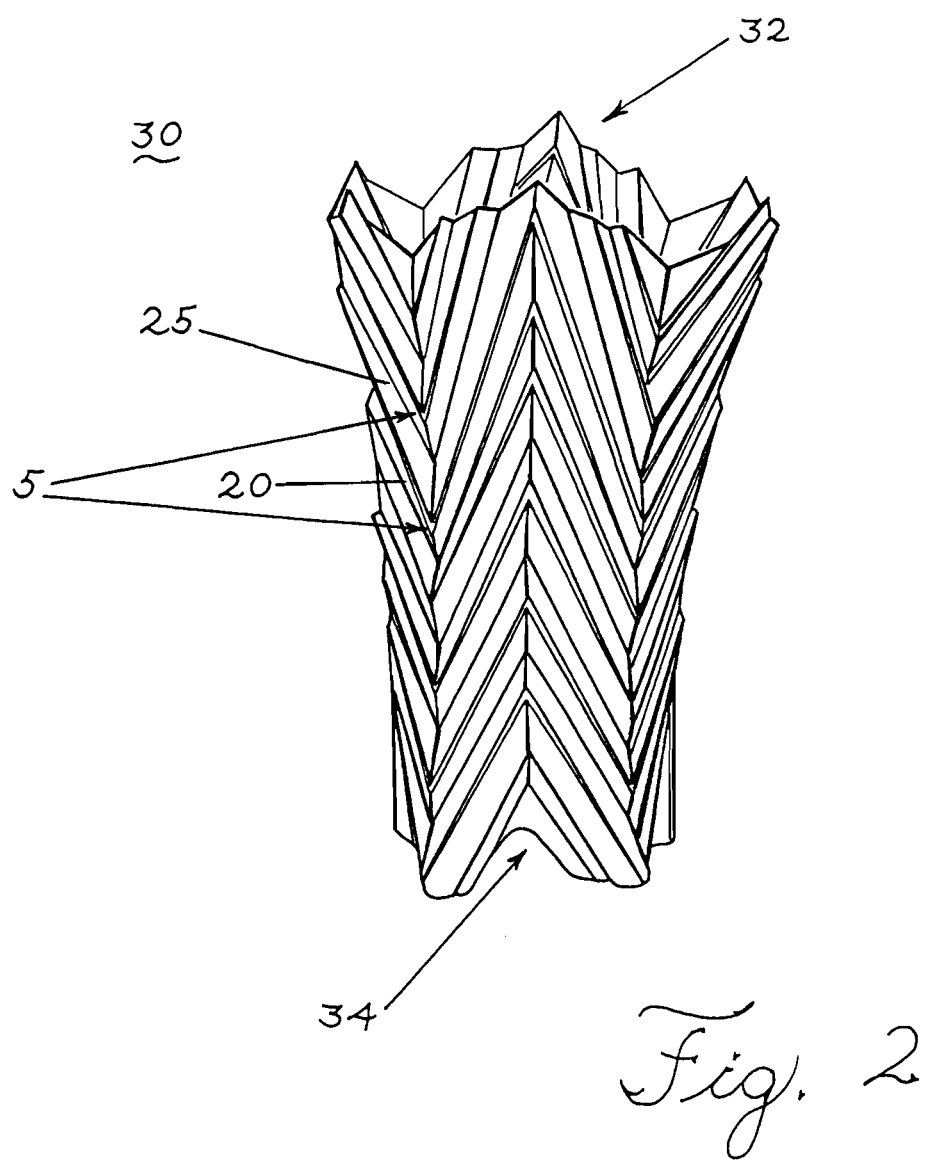
FIG. 2 is an illustration of the pattern shaped into a tubular shape for use as an endoluminal prosthesis.

FIG. 2 shows an endoluminal prosthesis of tubular graft material having a proximal end and a distal end. Graft material with the pattern described above can be given a tubular shape comprising a plurality of rows of folds that extend transversely around the prosthesis in an undulating pattern. A sheet of graft material rolled to form a tube using adhesive or stitching or some other form known in the art. Although not shown, at least one stent can be attached to at least one row of folds. The rows of folds allow for radial expansion and contraction of the endoluminal prosthesis, which enables the prosthesis to be deployed using a standard stent delivery system.

When arranged in a tubular shape, the rows 5 of folds allow the prosthesis to be expanded and contracted. As such, the tubular prosthesis can be balloon expandable or self-expanding. The patterns of the present invention also allow for easy loading into an introducer system. The prosthesis can fit into up to a 25 french delivery sheath when contracted.

Wire stents can be added to the prosthesis to provide stability and support. It may be preferred that a Z-stent is used and attached along the ridge 20 of the rows of folds. As a tubular prosthesis, the graft material has an exterior and an interior. When implanted in an endoluminal vessel, the exterior of the graft material faces the vessel wall while the interior borders the blood flow. The stents can be attached by stitching or adhesives or by any process currently known in the art. Stents can be attached to the graft material at different points, including the apices or the trough of the stent. It may be preferable to attach the stent to the pattern of graft material along the ridge of the row of folds.

The pattern can further comprise two sets of rows of folds with bias spacing. Bias spacing is when the distance between the ridge and the valley of a row is greater or smaller than the distance between ridges and valleys in a second set of rows. The distance between a ridge and a valley can be from about 0.3 cm to about 1 cm. The distance between a ridge 20 and a valley 25 in a first set of rows can be from about 0.5cm to about 1 cm. The distance between a ridge 50 and a valley 55 in a second set of rows can be from about 0.25 cm to about 1 cm.

Figure 3:
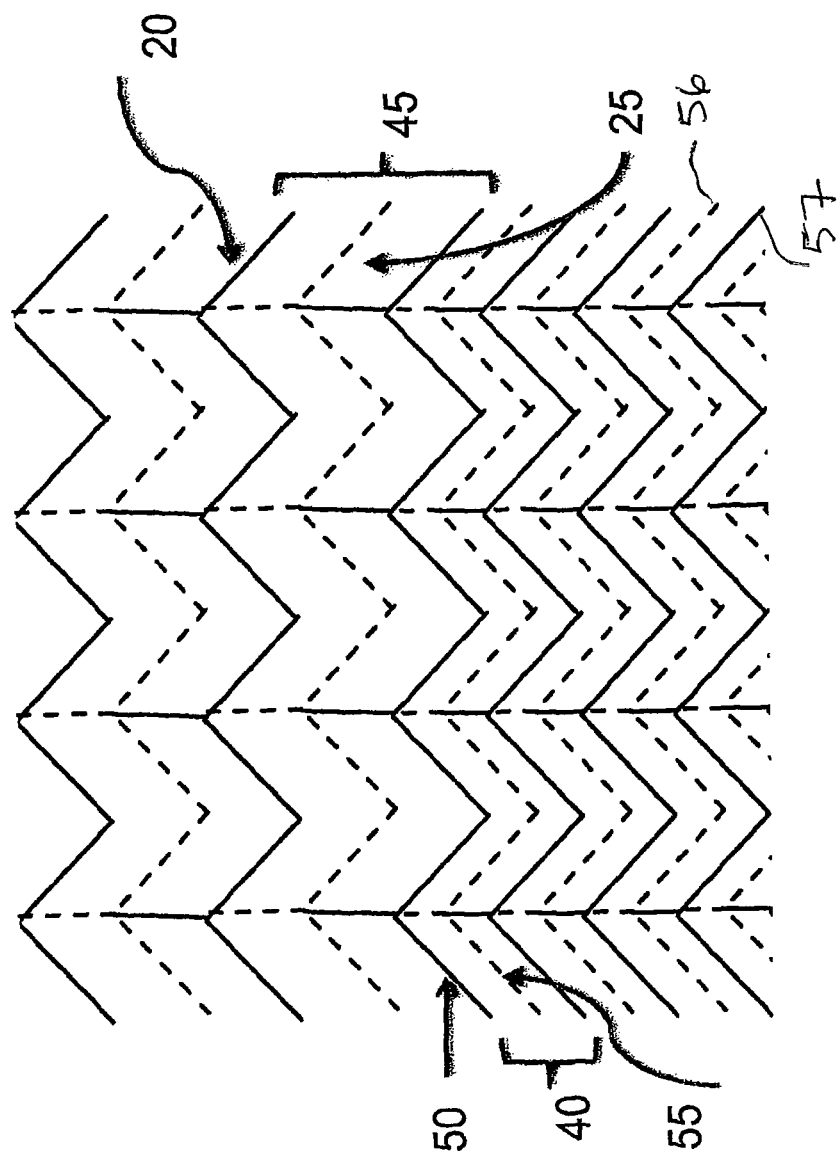
FIG. 3 is a section of the graft material having folds in a biased spacing.

Bias spacing is illustrated in FIG. 3 by a first set of rows 45 of folds where the ridge 20 and the valley 25 are separated by a first distance and a second set of rows 40 of folds where the ridge 50 and the valley 55 are separated by a second distance. The distance between ridge 50 and valley 55 in row 40 is greater than the distance between ridge 20 and valley 25 in row 45. Although two of the first set of rows 45 is placed consecutively in FIG. 3, rows of the first set of rows 45 can be separated by a row or two of the second set of rows 40. It may be preferred that a first set of rows 45 be placed on the distal and proximal ends of a tubular prosthesis formed by the pattern disclosed in this description.

With bias spacing, stents can be attached to the second set of rows 40 of folds to provide added support and strength to those areas of the prosthesis. Such areas will be stronger given the higher abundance of stent placement. The areas having a first set of rows 45 of folds will provide more flexibility than the areas with the more dense second set of rows 40.

It may be preferred that the first set of rows 45 of the folds with bias spacing be used at the proximal or endoluminal ends of an endoluminal prosthesis. The bias spacing portion can be useful as an overlap ends of an endoluminal prosthesis is mated with another stent graft. The wider spacing allows for a smoother seal between the two grafts, which helps reduce the risk of an endoleak. The first set of rows 45 can provide added support to the distal and proximal ends of a tubular prosthesis by further comprising stents or anchoring barbs. It may be preferred that the stents 56 be attached to the internal side of the tubular prosthesis along on the valleys 55. In this configuration, the external side of the bias spaced section can have a smooth seal with the mating end of another prosthesis. Other stents 57 then can be attached externally to the middle portion of the prosthesis. As such, at least one stent can be attached to the exterior of the tubular graft material and at least one stent can be attached to the exterior of the tubular graft material.

It is therefore intended that the foregoing detailed description be regarded as illustrative rather than limiting, and that it be understood that it is the following claims, including all equivalents, that are intended to define the spirit and scope of this invention.

The invention claimed is:

1. An endoluminal prosthesis of tubular graft material comprising:
    a proximal end and a distal end and a longitudinal axis from the proximal end to the distal end, the graft material comprising a plurality of horizontal rows of folds, the horizontal rows extending around the prosthesis in an nonhelical undulating pattern, wherein the plurality of rows extend perpendicularly to the longitudinal axis, the rows of folds each comprising at least one ridge and a valley, and
    a plurality of separate and discrete nonhelical stents each having an undulating configuration, where one stent of the plurality of stents is attached to a ridge of a row of folds and the other stent of the at least two stents is independently attached to another ridge of a row of folds, and the rows of folds allow for radial expansion and contraction of the prosthesis, wherein the undulating configuration of the stent mirrors the undulating pattern of the graft material, wherein no portion of any of the plurality of stents crosses a ridge or a valley of any fold of the undulating pattern of folds of the plurality of horizontal rows of folds in the graft material.

2. The endoluminal prosthesis of claim 1 where the at least two stents are attached to ridges of two nonconsecutive rows of folds.

3. The endoluminal prosthesis of claim 1 where the plurality of stents each comprises at least one apex and is attached to the graft material at the at least one apex.

4. The endoluminal prosthesis of claim 1 where the graft material comprises woven, non-woven, braided, or knitted material.

5. The endoluminal prosthesis of claim 1 where the tubular graft has an exterior and an interior and a stent attached to the interior of the tubular graft of the tubular graft material.

6. The endoluminal graft of claim 5 further comprising at least one stent attached to the exterior of the tubular graft material.

7. The endoluminal prosthesis of claim 1 further comprising a first set of rows of folds separated by a first distance and a second set of rows of folds separated by a second distance.

8. The endoluminal prosthesis of claim 1 comprising any two or more of the following:
    at least two stents are attached independently of each other to separate rows of folds where the separate rows of folds are two nonconsecutive rows of folds;
    at least one stent comprises at least one apex and is attached to the graft material at the at least one apex;
    the endoluminal prosthesis is balloon expanding or self-expanding;
    the tubular graft material has an exterior and an interior and stent is attached to the interior;
    at least one stent attached to the interior of the tubular graft material and at least one stent attached to the exterior of the tubular graft material;
    and a first set of rows of folds separated by a first distance and a second set of rows of folds separated by a second distance.

9. A nonhelical and horizontal pattern of folds in a graft material that allow for radial expansion and contraction comprising:
    a plurality of rows of folds having an undulating configuration with at least one apex and at least one trough and the rows of folds each comprising a ridge and a valley therein;
    a plurality of separate and discrete stents each having a nonhelical undulating configuration with at least one apex and one trough,
    where each stent of the plurality of stents is attached to at least one row of folds and conforms to the undulating configuration of a row of folds,
    where the graft material has a longitudinal axis and the rows are perpendicular to the longitudinal axis, and
    wherein no portion of any of the plurality of stents crosses a ridge or a valley of any fold of the undulating configuration in the graft material.

10. The pattern of claim 9 where the graft material has a tubular shape.

11. The pattern of claim 9 where the at least two stents are attached independently to two nonconsecutive rows.

12. The pattern of claim 9 where at least one stent is attached to at least one row of folds along the ridge of the row of folds.

13. The pattern of claim 9 where the graft material comprises woven, non-woven, braided, or knitted material.

14. The pattern of claim 9 further comprising a first set of rows of folds separated by a first distance and a second set of rows of folds separated by a second distance.

15. The pattern of claim 9 comprising any two or more of the following:
    where the graft material has a tubular shape;
    where at least two stents are attached independently to at least two nonconsecutive rows;
    where at least one stent is attached to at least one row of folds along the ridge of the row of folds;
    where the graft material comprises woven, non-woven, braided, or knitted material;
    and further comprising a first set of rows of folds separated by a first distance and a second set of rows of folds separated by a second distance.

* * * * *